(12) United States Patent
Lim et al.

(10) Patent No.: US 12,359,189 B2
(45) Date of Patent: Jul. 15, 2025

(54) NUCLEIC ACID PURIFICATION METHOD

(71) Applicant: CJ CHEILJEDANG CORPORATION, Seoul (KR)

(72) Inventors: Hwayeon Lim, Seoul (KR); Min Jong Kim, Seoul (KR); Changyub Oh, Seoul (KR); Il Chul Kim, Seoul (KR); Gyeonghwan Kim, Seoul (KR); Yu Shin Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 666 days.

(21) Appl. No.: 17/778,406

(22) PCT Filed: Sep. 9, 2020

(86) PCT No.: PCT/KR2020/012166
§ 371 (c)(1),
(2) Date: May 19, 2022

(87) PCT Pub. No.: WO2021/101042
PCT Pub. Date: May 27, 2021

(65) Prior Publication Data
US 2023/0017180 A1 Jan. 19, 2023

(30) Foreign Application Priority Data
Nov. 20, 2019 (KR) ........................ 10-2019-0149798

(51) Int. Cl.
*C12Q 1/6806* (2018.01)
*C12N 15/10* (2006.01)
*C30B 7/04* (2006.01)

(52) U.S. Cl.
CPC ....... *C12N 15/1003* (2013.01); *C12Q 1/6806* (2013.01); *C30B 7/04* (2013.01)

(58) Field of Classification Search
None
See application file for complete search history.

(56) References Cited

U.S. PATENT DOCUMENTS

| | | | |
|---|---|---|---|
| 7,176,305 B2 * | 2/2007 | Uchida | .................. C07H 19/20 536/26.1 |
| 2012/0184725 A1 | 7/2012 | Forman et al. | |
| 2019/0345480 A1 | 11/2019 | Bair et al. | |

FOREIGN PATENT DOCUMENTS

| | | |
|---|---|---|
| CN | 100395256 C | 6/2008 |
| CN | 101654469 A | 2/2010 |
| CN | 101863943 B | 10/2010 |
| CN | 101993466 B | 3/2011 |
| JP | S45-17578 B | 6/1970 |
| JP | 2004-175669 A | 6/2004 |
| KR | 10-0025552 B1 | 6/1988 |
| KR | 10-0054324 B1 | 9/1992 |
| KR | 10-0083595 B1 | 4/1995 |
| KR | 10-0117428 B1 | 7/1997 |
| KR | 10-2004-0045332 A | 6/2004 |
| KR | 2004-0045332 A | 6/2004 |
| KR | 10-2008-0007985 A | 1/2008 |
| KR | 10-0866273 B1 | 11/2008 |

OTHER PUBLICATIONS

English translation of the International Search Report of PCT/KR2020/012166 mailed Jan. 7, 2021; 2 pages.
Notice of Reasons for Refusal of Japanese Patent Application No. 2022-528719 mailed Apr. 24, 2023, together with the English translation; 13 pages.
1st Office Action of Indian Patent Application No. 2022217034322 mailed Sep. 15, 2023; 5 pages.
First Office Action of Brazilain Patent Application No. 112022096658 dated Oct. 31, 2023; 10 pages.

* cited by examiner

*Primary Examiner* — Patrick T Lewis
(74) *Attorney, Agent, or Firm* — Squire Patton Boggs (US) LLP

(57) ABSTRACT

The present application relates to a nucleic acid purification method, specifically to a nucleic acid purification method which includes a first step of crystallizing the nucleic acid using a solution containing a hydrophilic organic solvent; and a second step of drying the crystallized nucleic acid with high-humidity hot air.

6 Claims, 1 Drawing Sheet

[FIG. 1]
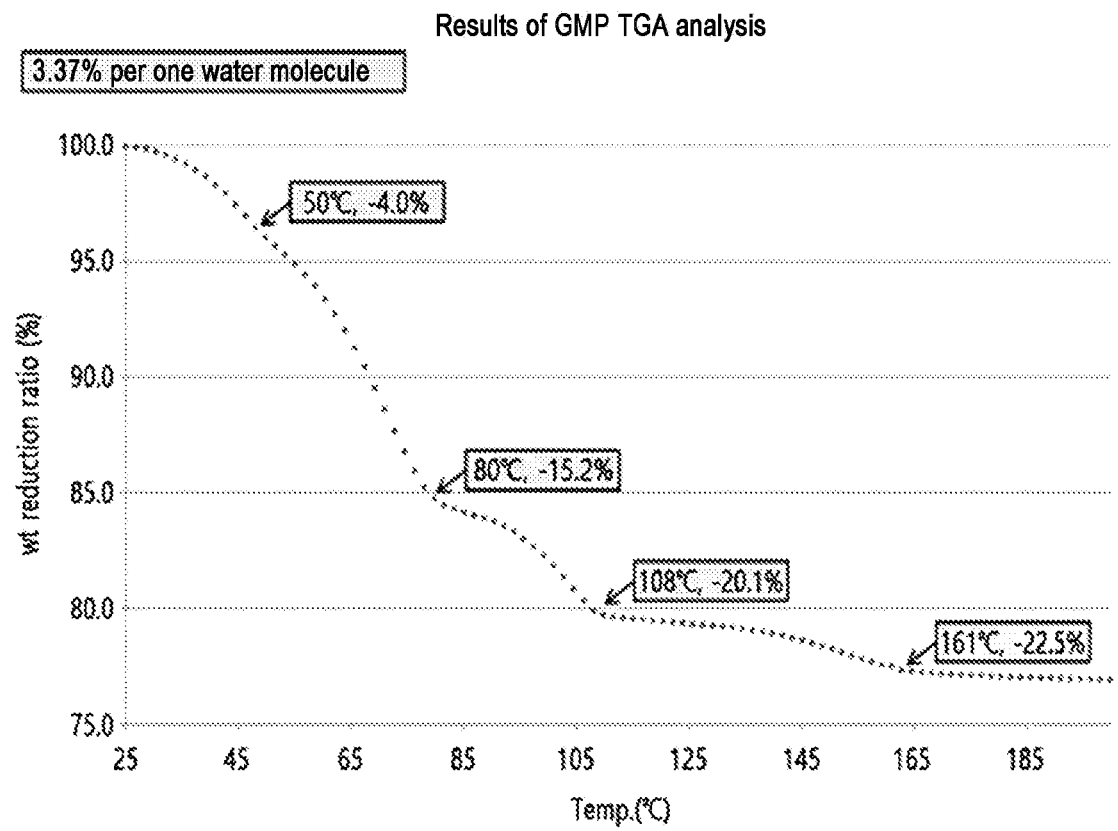
[FIG. 2]
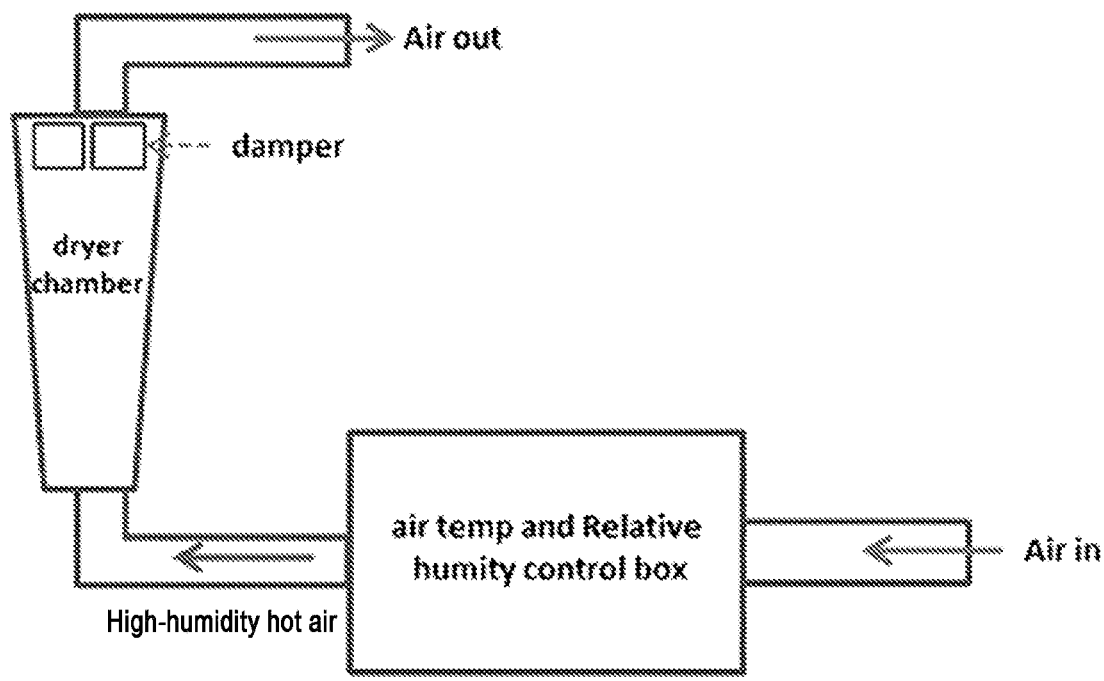

NUCLEIC ACID PURIFICATION METHOD

CROSS-REFERENCE TO RELATED APPLICATIONS

The present application is a 35 U.S.C. § 371 national-phase filing of International Application No. PCT/KR2020/012166, filed on Sep. 9, 2020, which claims the benefit of Korean Patent Application No. 10-2019-0149798, filed on Nov. 20, 2019, both of which applications are incorporated herein by reference in their entirety.

TECHNICAL FIELD

The present application relates to a nucleic; acid purification method, specifically to a nucleic acid purification method which includes a first step of crystallizing the nucleic acid using a solution containing a hydrophilic organic solvent; and a second step of drying the crystallized nucleic acid with high-humidity hot air.

BACKGROUND ART

As nucleic acid crystallization methods, a method using a hydrophilic organic solvent is mainly used. In the case of nucleic acids used for food, the removal of organic solvents in the final products is a significantly important issue because of the regulations on the residual amount of organic solvents by country. Hydrophilic organic solvents commonly used for nucleic acid crystallization include ethanol, methanol and the like. In particular, complete removal of methanol is required since the regulation on the residual amount of methanol is strict. Nevertheless, a method using an organic solvent (Korean Patent No. 10-0051324) is still generally used as a nucleic acid crystallization method. In this regard, in addition to the patent, Korean Patent No. 10-0083595, Chinese Patent No. 100395256, Chinese Patent No. 101863943, Korean Patent No. 10-0025552, and Korean Patent No. 10-0117428 and the like also disclose nucleic acid crystallization methods using an organic solvent.

Nucleic acid crystals, especially guanosine 5'-monophosphate disodium salt heptahydrate crystals that exist in the form of heptahydrate, lose water of crystallization at low temperatures such as room temperature as well, and a loss of about 70% occurs as heptahydrate is converted to 2.5 hydrate when the temperature is raised from room temperature to 80° C. for about 30 minutes (FIG. 1). This loss of hydrate in the guanosine 5'-monophosphate disodium salt heptahydrate crystals decreases the crystallinity of the crystals and causes crystal weakening and changes in crystal form, and it is thus significantly important to maintain the water of crystallization at the heptahydrate level during drying. When a large amount of surface water is present, crystals are transformed into an amorphous form, agglomeration occurs, and thus loss due to the agglomeration phenomenon also occurs during the purification process.

Because of these properties of nucleic acids, drying has been carried out at low temperatures such as room temperature as a method to remove the residual organic solvent in the crystallized nucleic acid. However, there is a problem in that the residual organic solvent in the crystals is not completely removed in the case of drying nucleic acid crystals at a low temperature. On the other hand, it is advantageous to perform drying at a high temperature to completely remove the residual organic solvent in the crystals in terms of organic solvent removal, but there is a problem in that the product quality of nucleic acid crystals decreases because of the evaporation of water of crystallization, and an alternative to this is needed.

DISCLOSURE

Technical Problem

An object of the present application is to provide a nucleic acid purification method which includes a first step of crystallizing the nucleic acid using a solution containing a hydrophilic organic solvent; and a second step of drying the crystallized nucleic acid with air having a temperature of 30° C. or more and 90° C. or less and a relative humidity of 40% or more and 90% or less.

Technical Solution

Each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description below.

Further, those skilled in the art will recognize, or be able to ascertain using no more than routine experimentation, many equivalents to the specific embodiments of the invention described herein. Further, these equivalents should be interpreted to fall within the scope of the present invention.

In addition, throughout this specification, when a part is referred to as "including" an element, it will be understood that other elements may be further included rather than other elements being excluded unless content to the contrary is specially described.

Hereinafter, the present invention will be described in detail.

In order to achieve the object, an aspect of the present application provides a nucleic acid purification method which includes a first step of crystallizing the nucleic acid using a solution containing a hydrophilic organic solvent; and a second step of drying the crystallized nucleic acid with air having a temperature of 30° C. or more and 90° C. or less and a relative humidity of 40% or more and 90% or less.

The nucleic acid purification method of the present application includes a first step of crystallizing the nucleic acid using a solution containing a hydrophilic organic solvent. In the present application, the crystallization method is not particularly limited as long as it is a method using a solution containing a hydrophilic organic solvent.

As used herein, the term "nucleic acid" refers to a compound consisting of a base, a sugar, and a phosphoric acid. Specifically, in the present application, the nucleic acid may be any one or more selected from the group consisting of guanosine 5'-monophosphate (5'-GMP) and inosine 5'-monophosphate (5'-IMP), more specifically guanosine 5'-monophosphate (5-GMP), but is not limited thereto.

In the present application, the nucleic acid is meant to include both salts of nucleic acid compounds and hydrate forms of the salts.

As used herein, the term "salt" refers to a form in which a cation and an anion are bonded to each other by electrostatic attraction, and may generally be a metal salt, a salt with an organic base, a salt with an inorganic acid, a salt with an organic acid, a salt with a basic or acidic amino acid, and the like. For example, the metal salt may be an alkali metal salt (sodium salt, potassium salt, or the like), an alkaline earth metal salt (calcium salt, magnesium salt, barium salt, or the like), an aluminum salt, or the like; the salt with an organic base may be a salt with triethylamine, pyridine, picoline, 2,6-lutidine, ethanolamine, diethanolamine, triethanolamine, cyclohexylamine, dicyclohexylamine, N,N-dibenzylethylenediamine, or the like; the salt with an inorganic acid may be a salt with hydrochloric acid, hydrobromic acid, nitric acid, sulfuric acid, phosphoric acid, or the like; the salt with an organic acid may be a salt with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, or the like; the salt with a basic amino acid may be a salt with arginine, lysine, ornithine, or the like; and the salt with an acidic amino acid may be a salt with aspartic acid, glutamic acid, or the like.

As used herein, the term "hydrate" refers to a form in which water is bonded to a compound, and water contained therein is called water of crystallization when the hydrate is a crystal.

In other words, in the present application, the nucleic acid refers to a nucleic acid compound, a salt thereof, or a hydrate of the salt. Specifically, the nucleic acid may be any one or more selected from the group consisting of guanosine 5'-monophosphate disodium salt (5'-GMP 2Na) and inosine 5'-monophosphate disodium salt (5'-IMP 2Na) that are a salt of guanosine 5'-monophosphate (5'-GMP) and a slat of inosine 5'-monophosphate (5'-IMP), respectively. More specifically, the nucleic acid may be guanosine 5'-monophosphate disodium salt (5'-GMP 2Na), but is not limited thereto.

Specifically, the nucleic acid may be hydrates of guanosine 5'-monophosphate disodium salt (5'-GMP 2Na) and inosine 5'-monophosphate disodium salt (5'-IMP 2Na). Specifically, the nucleic acid may be guanosine 5'-monophosphate disodium salt heptahydrate (5'-GMP 2Na 7$H_2O$) or inosine 5'-monophosphate disodium salt 7.5 hydrate (5'-IMP 2Na 7.5$H_2O$), but is not limited thereto.

As used herein, the term "hydrophilic organic solvent" refers to an organic solvent exhibiting hydrophilic properties. Specifically, the organic solvent may be any one or more selected from the group consisting of methanol and ethanol, more specifically methanol, but is not limited thereto.

The first step of the present application may specifically include a step (i) of adding a solution containing a hydrophilic organic solvent to a nucleic acid concentrate; a step (ii) of cooling the nucleic acid concentrate to which the solution is added; a step (iii) of separating the produced nucleic acid crystal slurry by centrifugation; and a step (iv) of washing the isolated nucleic acid crystals, but is not limited thereto.

In the present application, the hydrophilic; organic solvent may be added at 1.0 RV or more and 1.5 RV or less, specifically at 1.0 RV or more and 1.5 RV or less, 1.1 RV or more and 1.4 RV or less, 1.1 RV or more and 1.3 RV or less, or 1.15 RV or more and 1.25 RV or less with respect to the nucleic acid concentrate, but is not limited thereto.

In the present application, the cooling may be performed for 1 hour or more and 3 hours or less, specifically for 1 hour or more and 3 hours or less, or 1.5 hours or more and 2.5 hours or less, but is not limited thereto.

In the present application, the cooling may be performed at 20° C. or more and 30° C. or less, specifically at 20° C. or more and 30° C. or less, 22° C. or more and 28° C. or less, 23° C. or more and 27° C. or less, or 24° C. or more and 26° C. or less, but is not limited thereto.

In the present application, the centrifugation may be performed at 2000 rpm or more and 3000 rpm or less, but is not limited thereto.

The nucleic acid purification method of the present application includes a second step of drying the crystallized nucleic acid with air having a temperature of 30° C. or more and 90° C. or less and a relative humidity of 40% or more and 90% or less.

The second step of the present application may specifically include a step (a) of controlling the temperature and humidity of the air; and a step (b) of drying the nucleic acid crystals obtained in the first step with temperature and humidity-controlled air, but is not limited thereto.

In the present application, the air may have a temperature of 30° C. or more and less than 60° C. and a relative humidity of 40% or more and 90% or less. Specifically, the temperature may be 30° C. or more and less than 60° C., 30° C. or more and 55° C. or less, 35° C. or more and 55° C. or less, 35° C. or more and 50° C. or less, 40° C. or more and 55° C. or less, 45° C. or more and 55° C. or less, more than 45° C. and 55° C. or less, 45° C. or more and less than 60° C., or 50° C. or more and less than 60° C., and the relative humidity may be 40% or more and 90% or less. 55% or more and 85% or less, 50% or more and 80% or less. 40% or more and 60% or less, 45% or more and 55% or less, or 80% or more and 90% or less, but the temperature and the relative humidity are not limited thereto.

In the present application, the air may have a temperature of 60° C. or more and 90° C. or less and a relative humidity of 70% or more and 90% or less. Specifically, the temperature may be 60° C. or more and 90° C. or less, 60° C. or more and 85° C. or less, 60° C. or more and 80° C. or less, 65° C. or more and 90° C. or less, 65° C. or more and 80° C. or less, or 65° C. or more and 75° C. or less, and the relative humidity may be 70% or more and 90% or less, 75% or more and 90% or less, or 80% or more and 90% or less, but the temperature and the relative humidity are not limited thereto.

In the present application, the drying may be performed for 2 hours or more and 7 hours or less. Specifically, the drying time may be 2 hours or more and 7 hours or less, 2.5 hours or more and 6.5 hours or less, 3 hours or more and 6 hours or less, but is not limited thereto.

In the present application, the drying method is not particularly limited as long as it is a method using high-humidity hot air, namely, temperature- and humidity-controlled air. Specifically, the drying may be performed using a dryer capable of controlling the humidity of the air, but is not limited thereto.

The dryer used in the present application is composed of a temperature and humidity control device and a dryer chamber (FIG. 2). High-humidity hot air of which the temperature and humidity are controlled by the temperature and humidity control device may be supplied to the dryer chamber, and then wet crystals may be introduced to remove the organic solvent and surface water in the nucleic acid crystals. FIG. 2 is a schematic diagram illustrating an example of a dryer usable in the present application.

Advantageous Effects

In the nucleic acid purification method of the present application, the organic solvent remaining after nucleic acid crystallization using a hydrophilic organic solvent can be completely removed through drying with high-humidity hot air. The water of crystallization in nucleic acids is maintained during drying as well, the hydrate structure is maintained, and the agglomeration of crystals does not occur, and thus an excellent yield is obtained.

The effects can be exhibited only through drying with high-humidity hot air, thus there is also a cost reduction effect, and the nucleic acid purification method can be widely utilized for more economical purification of nucleic acids.

BRIEF DESCRIPTION OF DRAWINGS

FIG. 1 is a graph illustrating the loss of water of crystallization in nucleic acid crystals depending on the temperature; and FIG. 2 is a schematic diagram illustrating an example of a dryer usable in the present application.

DETAILED DESCRIPTION OF THE INVENTION

Hereinafter, the configuration and effects of the present invention will be described in more detail with reference to exemplary embodiments. However, these exemplary embodiments are for illustrative purposes only, and the scope of the present invention is not intended to be limited by these exemplary embodiments.

EXPERIMENTAL EXAMPLE 1

Experimental Example 1-1. Crystallization of Nucleic Acid

A concentrate was prepared in which guanosine 5'-monophosphate disodium salt heptahydrate was present at about 250 g/L. A hydrophilic organic solvent corresponding to 1.2 RV (relative volume) with respect to the volume of the concentrate was added at a flow velocity of 0.2 RV/hr at 38° C. for 6 hours. Cooling was performed to 25° C. for 2 hours from the time point at which the input was terminated, and the crystal slurry was separated using a centrifuge. At this time, centrifugation was performed at a speed of 2000 rpm to 3000 rpm, an aqueous solution containing a hydrophilic organic solvent at 50% was used as the washing solution, and the crystals were washed through spraying at 2000 rpm. After washing was completed, wet crystals of guanosine 5'-monophosphate disodium salt heptahydrate having a moisture content of 30% was obtained.

Experimental Example 1-2. Drying of Crystallized Nucleic Acid

The high-humidity hot air used for crystal drying was controlled using a humidity control device installed at the bottom of the dryer (FIG. 2). After low-temperature air was heated to a high temperature, the humidity was controlled for use. After stabilization by the humidity control device, the high-humidity hot air was supplied to the dryer chamber. Thereafter, the wet crystals obtained in Experimental Example 1-1 was introduced to remove the organic solvent and surface water in the nucleic acid crystals. The temperature and humidity inside the dryer were observed using a thereto-hygrometer installed inside the chamber.

EXPERIMENTAL EXAMPLE 2. CRYSTAL ANALYSIS

Experimental Example 2-1. Analysis of Change in Organic Solvent Content

Equipment: Hewlett 5890 Packard series 2
Column: Porapak q (waters associates, 6 FT ⅛ in ⁸⁰⁄₁₀₀ packed column supelco)
Carrier gas: hydrogen, nitrogen
Detector type: FLD
Oven temperature: 140° C.
Sample inlet temperature: 150° C.
Detector temperature: 175° C.
Sample injection volume: 1 µL In order to analyze the organic solvent content in crystals, guanosine 5'-monophosphate disodium salt heptahydrate crystals were precisely weighed by 1.0000 g, placed in a 0.01 L volumetric flask, and diluted with ultrapure water to prepare a 100 g/L sample. Thereafter, methanol (or ethanol) standard reagent (J.T. Baker>99.0%) was prepared at 50 mg/L, the standard reagent was used as an external standard, and the sample was analyzed by gas chromatography (GC).

Experimental Example 2-2. Analysis of Change in Water of Crystallization Through Measurement of Residual Hydrate In order to analyze the residual hydrate content, guanosine 5'-monophosphate disodium salt heptahydrate crystals were precisely weighed by 20 mg and placed in a thermogravimetric analyzer pan. Thereafter, the temperature of the thermogravimetric analyzer was raised from the initial temperature of 25° C. to 300° C. at a rate of 2° C./min to observe the weight change. At this time, in the guanosine 5'-monophosphate disodium salt heptahydrate crystals, a weight change of 23.6% occurs in the about 200° C. zone, this can be considered as a weight change due to evaporation of the heptahydrate, and the residual hydrate content was analyzed through this.

Experimental Example 2-3. Analysis of Yield Change

In order to analyze the yield after drying, the loss occurred during drying was measured by measuring the weight of the fine powder collected in the bag filter mounted on the top of the dryer after drying was completed.

EXPERIMENTAL EXAMPLE 3. OBSERVATION OF CHANGE IN WATER OF CRYSTALLIZATION DEPENDING ON TEMPERATURE AND HUMIDITY CONDITION

Changes in water of crystallization in the guanosine 5'-monophosphate disodium salt heptahydrate wet crystals were observed while changing the temperature and humidity conditions in the dryer chamber by the humidity control device installed at the bottom of the dryer.

As a result, as presented in Table 1, the residual hydrate was found to be 12.7% to 25.2% when drying was performed under the conditions of a temperature of 30° C. or more and 90° C. or less and a relative humidity of 40% or more and 90% or less.

The residual hydrate was confirmed to be 21.4% to 25.2% particularly when drying was performed under conditions of a temperature of 30° C. or more and less than 60° C. and a relative humidity of 40% or more or a temperature of 60° C. or more and 90° C. or less and a relative humidity of 80% or more, and it has been thus confirmed that a remarkably greater amount of residual hydrate is present in the above ranges.

TABLE 1

| Moisture(%) | | Temperature (° C.) | | |
|---|---|---|---|---|
| | | 36 | 50 | 70 |
| Relative humidity (RH) | 10 | 8.8 | 7.6 | 5.4 |
| | 50 | 25.2 | 21.9 | 12.7 |
| | 60 | 24 | 21.4 | 13.4 |
| | 70 | 22.1 | 20.6 | 13.5 |
| | 75 | 23.7 | 22.7 | 13.9 |
| | 80 | 24 | 24 | 21.4 |

Through the results, it has been found that the water of crystallization is maintained during long-term treatment in the dryer as well under the temperature and humidity conditions. Since the hydrate structure was not deformed during the drying process as the water of crystallization was about 23.6% (±2%), which is the theoretical amount of water of crystallization in the guanosine 5'-monophosphate disodium salt heptahydrate crystals, it has been confirmed that the agglomeration phenomenon of crystals does not occur, and there is no yield loss due to agglomeration. In addition, it has been confirmed that the crystallinity is also excellent since there is no overdrying process.

Through this, it has been confirmed that the water of crystallization is maintained step by step, and complete removal of the organic solvent is possible when the temperature and relative humidity are within the ranges, and the agglomeration phenomenon of crystals does not occur, and there is no yield loss due to agglomeration since the hydrate structure is not deformed during the drying process.

Example 1. Nucleic Acid Purification I

After the temperature and humidity in the dryer chamber were kept constant at 35° C. and 50% by the humidity control device installed at the bottom of the dryer, guanosine 5'-monophosphate disodium salt heptahydrate wet crystals were continuously introduced. At this time, the moisture, including the surface water and the water of crystallization, in the wet crystals was about 30%.

As a result, as presented in Table 2, the residual hydrate was 22.3%, and the methanol content was 0 ppm when drying was performed for 6 hours under the conditions of a temperature of 34° C. and a relative humidity of 48%.

TABLE 2

| | Operation conditions | | | Results of crystal analysis | |
|---|---|---|---|---|---|
| Time | Temperature and humidity inside dryer | | Outlet DAMPER | | |
| Min | temp | RH | temp | Moisture % | MEOH ppm |
| 0 | 36 | 43 | 36 | 50 | 31 | 808 |
| 15 | 35 | 48 | 34 | 50 | 21 | 80.2 |
| 60 | 35 | 48 | 35 | 65 | 21.5 | 24.4 |
| 120 | 34 | 50 | 34 | 60 | 21.1 | 21.3 |
| 180 | 34 | 52 | 34 | 70 | 21.4 | 15.7 |
| 360 | 34 | 52 | 34 | 70 | 22.3 | N.D. |

From the results, it has been found that the water of crystallization is maintained step by step during drying, and the complete removal of methanol is possible under the temperature and humidity conditions. In addition, it has been confirmed that the agglomeration phenomenon of crystals does not occur, and there is no yield loss due to agglomeration since the hydrate structure is not deformed during the drying process.

Example 2. Nucleic Acid Purification II

After the temperature and humidity in the dryer chamber were kept constant at 55° C. and 60% by the humidity control device installed at the bottom of the dryer, guanosine 5'-monophosphate disodium salt heptahydrate wet crystals were continuously introduced. At this fine, the moisture, including the surface water and the water of crystallization, in the wet crystals was about 30%.

As a result, as presented in Table 3, the residual hydrate was 23% and the methanol content was 0 ppm when drying was performed for 3 hours under the conditions of a temperature of 55° C. and a relative humidity of 60%.

TABLE 3

| | Operation conditions | | | Results of crystal analysis | |
|---|---|---|---|---|---|
| Time | Temperature and humidity inside dryer | | Outlet DAMPER | | |
| Min | temp | RH | temp | Moisture % | MEOH ppm |
| 0 | 55 | 42 | 55 | 50 | 30 | 812 |
| 15 | 56 | 50 | 56 | 50 | 20 | 70 |
| 30 | 58 | 55 | 58 | 50 | 19 | 20 |
| 60 | 55 | 52 | 55 | 60 | 20 | 17 |
| 120 | 55 | 72 | 55 | 65 | 21 | 12 |
| 180 | 55 | 71 | 55 | 60 | 23 | N.D. |

From the results, it has been found that the water of crystallization is maintained step by step during drying, and the complete removal of methanol is possible under the temperature and humidity conditions. In addition, it has been confirmed that the agglomeration phenomenon of crystals does not occur, and there is no yield loss due to agglomeration since the hydrate structure is not deformed during the drying process.

Example 3. Nucleic Acid Purification III

After the temperature and humidity in the dryer chamber were kept constant at 70° C. and 80% by the humidity control device installed at the bottom of the dryer, guanosine 5'-monophosphate disodium salt heptahydrate wet crystals were continuously introduced. At this time, the moisture, including the surface water and the water of crystallization, in the wet crystals was about 30%.

As a result, as presented in Table 4, the residual hydrate was 23%, and the methanol content was 0 ppm when drying was performed for 3 hours under the conditions of a temperature of 70° C. and a relative humidity of 80%.

TABLE 4

| | Operation conditions | | | Results of crystal analysis | |
|---|---|---|---|---|---|
| Time | Temperature and humidity inside dryer | | Outlet DAMPER | | |
| Min | temp | RH | temp | Moisture % | MEOH ppm |
| 0 | 68 | 77 | 68 | 50 | 60 | 809 |
| 30 | 70 | 79 | 70 | 50 | 23 | 20 |
| 60 | 71 | 80 | 71 | 50 | 22 | 18 |

TABLE 4-continued

| Time | Operation conditions | | | | Results of crystal analysis | |
|---|---|---|---|---|---|---|
| | Temperature and humidity inside dryer | | Outlet | DAMPER | Moisture | MEOH |
| Min | temp | RH | temp | % | % | ppm |
| 90 | 71 | 80 | 71 | 50 | 22 | 15 |
| 120 | 71 | 80 | 71 | 50 | 23 | 12 |
| 150 | 71 | 80 | 71 | 50 | 21 | 6 |
| 180 | 70 | 81 | 70 | 60 | 23 | N.D. |
| 18 hr | 70 | 80 | 70 | 60 | 24 | N.D. |

From the results, it has been found that the water of crystallization is maintained step by step during drying, and the complete removal of methanol is possible under the temperature and humidity conditions. In addition, it has been confirmed that the agglomeration phenomenon of crystals does not occur, and there is no yield loss due to agglomeration since the hydrate structure is not deformed during the drying process.

Comparative Example 1. Nucleic Acid Purification IV

After the temperature (relative humidity-uncontrolled dry air; humidity of about 13%) in the dryer chamber was kept constant at 37° C. by the humidity control device installed at the bottom of the dryer, guanosine 5'-monophosphate disodium salt heptahydrate wet crystals were continuously introduced. At this time, the moisture, including the surface water and the water of crystallization, in the wet crystals was about 30%.

As a result, as presented in Table 5, the residual hydrate was 13%, and the methanol content was 9 ppm when drying was performed for 3 hours under the conditions of a temperature of 37° C. and an uncontrolled relative humidity (about 13%).

TABLE 5

| Time | Operation conditions | | | | Results of crystal analysis | |
|---|---|---|---|---|---|---|
| | Temperature and humidity inside dryer | | Outlet | DAMPER | Moisture | MEOH |
| Min | temp | RH | temp | % | % | ppm |
| 0 | 36 | 10 | 36 | 50 | 30 | 810 |
| 15 | 37 | 12 | 37 | 50 | 19 | 65 |
| 30 | 38 | 12 | 38 | 50 | 18 | 25 |
| 60 | 36 | 15 | 36 | 50 | 17 | 21 |
| 120 | 36 | 15 | 36 | 50 | 15 | 16 |
| 180 | 36 | 13 | 36 | 50 | 13 | 9 |

From the results, it has been found that the complete removal of methanol is not possible under the temperature and humidity conditions. In addition, it has been confirmed that the crystallinity is inferior since the water of crystallization is about 13%, and a loss of about 45% based on the theoretical amount of water of crystallization occurs, and the quality cannot be achieved due to an insufficient amount of hydrate.

Comparative Example 2 Nucleic Acid Purification V

After the temperature and humidity in the dryer chamber were kept constant at 70° C. and 50% by the humidity control device installed at the bottom of the dryer, guanosine 5'-monophosphate disodium salt heptahydrate wet crystals were continuously introduced. At this time, the moisture, including the surface water and the water of crystallization, in the wet crystals was about 30%.

As a result, as presented in Table 6, the residual hydrate was 13%, and the methanol content was 0 ppm when drying was performed for 3 hours under the conditions of a temperature of 37° C. and a relative humidity of 50%.

TABLE 6

| Time | Operation conditions | | | | Results of crystal analysis | |
|---|---|---|---|---|---|---|
| | Temperature and humidity inside dryer | | Outlet | DAMPER | Moisture | MEOH |
| Min | temp | RH | temp | % | % | ppm |
| 0 | 68 | 43 | 68 | 50 | 31 | 812 |
| 30 | 70 | 51 | 70 | 50 | 21 | 43 |
| 60 | 71 | 48 | 71 | 50 | 21 | 29 |
| 90 | 71 | 48 | 71 | 50 | 18 | 18 |
| 120 | 71 | 51 | 71 | 50 | 17 | 11 |
| 150 | 71 | 43 | 71 | 50 | 14 | 9 |
| 180 | 70 | 51 | 70 | 50 | 13 | N.D. |

From the results, it has been found that the complete removal of methanol is possible under the temperature and humidity conditions. However, it has been confirmed that the crystallinity is inferior since the water of crystallization is about 13%, and a loss of about 45% based on the theoretical amount of water of crystallization occurs, and the quality cannot be achieved due to insufficient amount of hydrate.

From the results described above, it has been found that the water of crystallization is maintained, methanol is completely removed, and there is no yield loss due to agglomeration of crystals when the temperature and humidity ranges of the present application, namely, the conditions of a temperature of 30° C. or more and 90° C. or less and a relative humidity of 40% or more and 90% or less are kept; specifically, a humidity of 40% or more and 90% or less is kept at a temperature of 30° C. or more and less than 60° C. and a humidify of 70% or more, and 90% or less is kept at a temperature of 60° C. or more and 90° C. or less. In addition, it has been found that the water of crystallization evaporates or the organic solvent cannot be completely removed because of the decrease in humidity when the temperature and humidity ranges are out of the above ranges.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims or equivalents of such metes and bounds are therefore intended to be embraced by the claims.

The invention claimed is:

1. A nucleic acid purification method, the method comprising:
   a first step of crystallizing the nucleic acid using a solution containing a hydrophilic organic solvent; and a second step of drying the crystallized nucleic acid with air having a temperature of 30° C. or more and 90° C. or less and a relative humidity of 40% or more and 90% or less.

2. The nucleic acid purification method of claim 1, wherein the nucleic acid includes any one or more selected from the group consisting of guanosine 5'-monophosphate disodium salt and inosine 5'-monophosphate disodium salt.

3. The nucleic acid purification method of claim 1, wherein the nucleic acid includes guanosine 5'-monophosphate disodium salt heptahydrate or inosine 5'-monophosphate disodium salt 7.5 hydrate.

4. The nucleic acid purification method of claim 1, wherein the hydrophilic organic solvent is any one or more selected from the group consisting of methanol and ethanol.

5. The nucleic acid purification method of claim 1, wherein the air has a temperature of 30° C. or more and less than 60° C. and a relative humidity of 40% or more and 90% or less.

6. The nucleic acid purification method of claim 1, wherein the air has a temperature of 70° C. or more and 90° C. or less and a relative humidity of 70% or more and 90% or less.

* * * * *